United States Patent [19]

Chalifoux

[11] Patent Number: 5,520,921

[45] Date of Patent: May 28, 1996

[54] PERIODONTAL PACKING DEVICE

[75] Inventor: Paul R. Chalifoux, Wellesley, Mass.

[73] Assignee: Wellesley Research Associates, Inc., Wellesley, Mass.

[21] Appl. No.: 189,654

[22] Filed: Feb. 1, 1994

[51] Int. Cl.⁶ .................................................. B29B 15/00
[52] U.S. Cl. .......................... 424/422; 424/435; 433/136; 433/138
[58] Field of Search .................................. 424/422, 435; 433/136, 138

[56] References Cited

U.S. PATENT DOCUMENTS 3,219,527  11/1965  Gurney ................................... 424/435
4,861,268  8/1989  Garay et al. ........................... 424/435

Primary Examiner—Mark D. Sweet
Attorney, Agent, or Firm—Paul J. Cook

[57] ABSTRACT

A periodontal packing device is provided comprising a plate having two through holes for a thread. A second set of holes can be provided for packing material. The thread is passed through the two through holes to form a thread loop adjacent one surface of the plate and two ends which are tied together adjacent a second surface of the plate.

38 Claims, 2 Drawing Sheets

PERIODONTAL PACKING DEVICE

BACKGROUND OF THE INVENTION

This invention relates to a periodontal packing device. More particularly, this invention relates to a periodontal packing device which is easy to apply, is effectively retained during use and is easily removed.

Subsequent to oral surgery where an incision is made, a packing material is applied to the area of incision in order to promote healing and reduce postoperative pain. The packing is generally formed from a solid, pliable material which is sedative and adhesive. A wide variety of devices have been utilized including a barrier which can be inserted in the spaces between teeth in order to retain the packing and over the incision and the barrier. These devices are undesirable since they rely upon adhesion between the packing the barrier. In practice, the adhesive forces retaining these dissimilar materials together are rapidly eliminated by normal mouth movement and by the reactive effects of saliva. In addition, such devices are difficult to administer and to remove, since they must rely upon mechanical means in addition to the adhesive forces in order to retain the packing in place. These mechanical means require forces to position the device and to remove the device. The use of such force is undesirable since its use increases the chances of injury to the patient. The mechanical retention which is passed between the teeth below the contact area damages remaining gingival tissue. In addition, the wire is twisted on the outside causing irritation to the check area.

Accordingly, it would be desirable to provide a periodontal packing device which substantially reduces or eliminates reliance solely upon a packing adhesion to retain the packing. In addition, it would be desirable to provide a periodontal device which can be positioned with a minimal mechanical force.

SUMMARY OF THE INVENTION

The present invention provides a periodontal packing device comprising a plate and flexible strand such as a rubber band or a thread extending through a pair of holes in the plate. The through holes for the strand on the plate are positioned so that the strand which forms a loop and acts as a fulcrum, assist in packing retention. After positiioning packing material, the strand is positioned between teeth and through packing material in a normal flossing manner such that the loop surrounds one or more teeth. The plate is slid down the strand and pressed into packing material. The strand is tightened and tied to retain the plate and the packing material. If desired, a second layer of packing material is applied over the plate and packing material. Adhesion of the second layer occurs to the plate and surrounding material from the first layer of packing. Removal is accomplished by cutting the strand or undoing a knot in the strand. In areas such as the back of the mouth or the lower jaw, it is desirable to have the knot to the outside of the teeth as part of the loop flossed between and around teeth. In addition, the tied strand which forms a loop on one side of the plate provides an important safety factor. If the plate is dropped in the mouth or down the throat, the plate is easily retrieved by grabbing the loose strand ends.

In an alternative embodiment, the plate is also provided with at least one hole through which packing material can extend through so that adhesive forces are formed between packing portions positioned on both opposing surfaces of the plate. In use, after placing the packing material, the strands, such as in the form of a dental floss, which comprise, for example, waxed thread, are passed between teeth positioned adjacent the oral area where it is desired to retain the plate. The strands are tightened to position and the plate is placed in intimate contact with the packing material. The slip knot is tightened. More knots are tied if more security from the knot coming undone and loose is required. In an alternative embodiment, a second portion of packing material then is applied to the exposed plate surface. A packing material extends through at least one hole in the plate so that the packing material portions are adhered to each other and assist in retaining the plate in the desired position. The second layer also covers the knot and excess thread so no irritation to the tongue occurs and so the knot remains secure.

In an alternative embodiment, two plates are used to retain packing material placed on the outside and inside of a row of teeth. The floss strand is looped through two holes of one plate. The ends are then passed through two holes of a second plate and a slip knot tied. The plates are placed on opposite sides of a row of teeth and the strand in between the plates flossed between the teeth forming a loop around a tooth or several teeth with a plate on either side. The thread loop is tightened so the plates are secure to packing material on the outside and the inside of a row of teeth.

The periodontal packing structure of this invention provides substantial advantages over the structures of the prior art. The structure is easily positioned since the strands, e.g., dental floss can be easily positioned between adjacent teeth with a minimum of mechanical force. When a second layer of material is used, the adhesive forces relied upon for retaining the structure are formed by adhering packing material to itself rather than to a different material. The plate provides a semibarrier to saliva on the packing directly adjacent the oral area of interest. The thread and plate effectively hold the packing in place. In addition, the packing and plate can be easily removed by removing the thread.

DESCRIPTION OF SPECIFIC EMBODIMENTS

In accordance with this invention, a periodontal structure if provided for use in conjunction with a packing material. The structure comprises a plate having through holes for a thread to pass through. The plate can also have at least one hole through which conventional packing composition can extend through during use.

The plate is formed from a solid material such as paper, plastic, metal or combinations of like materials. Preferably, the plate has a plurality of holes which allows the packing material to extend through the plate at a plurality of points. This arrangement promotes increased strength for retaining the plate in place.

The thread employed can be any common thread material as long as it does not cause adverse reaction to a patient. A preferred thread material is dental floss which generally is formed from a thread coated with a waxy composition which promotes insertion of the thread between adjacent teeth. The thread is passed through two holes in the plate to form a loop on one side of the plate. The loop then is positioned to encompass one or more teeth by positioning two portions of the loop between adjacent teeth. Loose ends of the thread are tied together adjacent the side of the plate opposite the side of the plate from which the loop extends. It is preferred that the loose ends of the thread be tied together with a slip knot. The slip knot provides a means for tightening the loop around the teeth to thereby increase the contact force between packing adjacent an incision and the plate. In addition, the slip knot provides a convenient means for subsequently reducing this contact force so that the plate and packing can be removed to permit additional dental work. The use of a thread rather than a plate or wire inserted between the teeth is desirable because its use reduces the amount of mechanical force needed to insert packing retention means between adjacent teeth.

Figure 1:
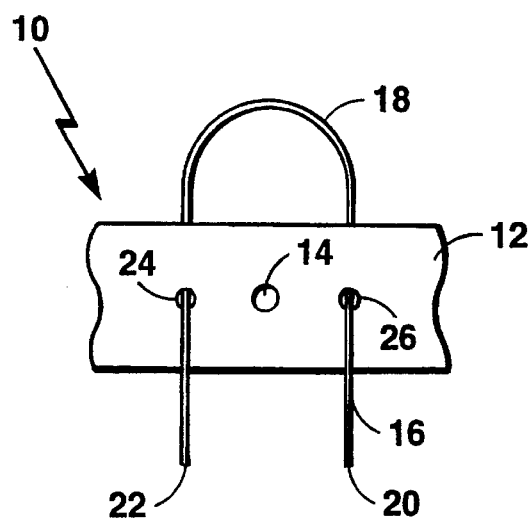
FIG. 1 is a perspective view of one embodiment of periodontal packing structure of this invention.

Referring to FIG. 1, the periodontal packing device 10 of this invention includes a plate 12 having at least one hole 14 which permits packing material to be passed therethrough and a thread 16. The thread 16 has a loop portion 18 and two end portions 20 and 22. The thread 16 is passed through two holes 24 and 26 in plate 12.

Figure 2:
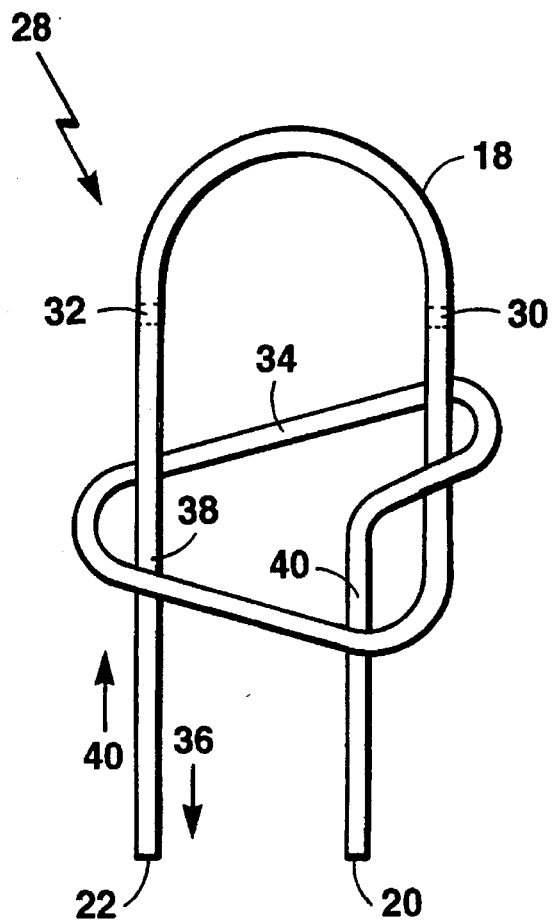
FIG. 2 shows a slip knot arrangement for the thread which can be utilized in the present invention.

Referring to FIG. 2, a conventional slip knot 28 is shown having a loop 18 and two ends 20 and 22. The plate (not shown) is positioned on loop 18 as shown in dotted sections 30 and 32. In use, the loop 18 is positioned around one or more teeth (not shown). End 22 is first pulled through secondary loop 34 in the direction shown by arrow 36 and secondary loop 34 is tightened so that thread sections 38 and 40 within the secondary loop 34 contact each other after packing material is positioned between an oral area, such as an area of incision and one side of the plate. By tightening the thread in this manner, the plate is secured in the desired position and the packing material is forced through at least one hole in the plate. Packing material can then be applied to a second surface of the plate as described in more detail below, if desired. When the use of the packing is completed, the thread 28 is loosened by moving end 22 in the direction shown by arrows 40 through the secondary loop 34 to loosen the force of thread 28 on the plate. The plate, thread and packing material then can be easily removed from the patient. Alternatively, loop 18 is cut and removal accomplished by pulling the packing material and plate resulting in the cut threads coming through the area between teeth.

Figure 3:
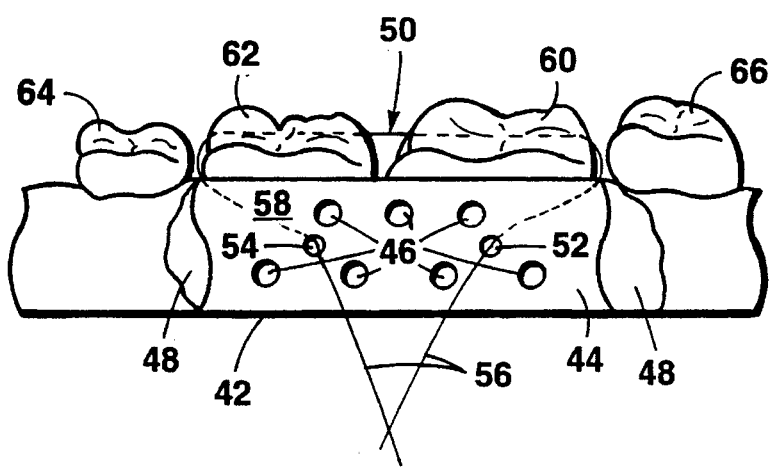
FIG. 3 shows an alternative structure from the plate portion of the structure of this invention.

Referring to FIG. 3, an alternative periodontal packing device 42 of this invention is shown. The device 42 includes a plate 44 having a plurality of holes 46 through which packing material 48 can be passed. A thread 50 is passed through holes 52 and 54 in plate 44 to form a loop on one side of the plate 44 and end sections 56 which are tied together in the opposing surface 58 of plate 44. The holes 52 and 54 are positioned at an intermediate height of plate 44 to function as a fulcrum about which the plate can move so that force is more evenly distributed over the plate and so that the plate can be forced against the packing 48 over substantially its entire surface. The loop 18 is positioned around teeth 60 and 62, between teeth 62 and 64 and between 60 and 66. The ends 56 are tightened together to force plate 44 into contact with packing 48. Additional packing then is applied to plate surface 58 to contact packing 48 extending through holes 46. The packing 48 and the newly applied packing (not shown) are then adhered together through holes 46 and around the periphery of plate 44. In addition, the packing material is adhered to both surfaces of the plate 44. The only mechanical device inserted between the teeth is the thread 50 which requires only minimal mechanical force as compared, for example with a plate like structure.

Figure 4:
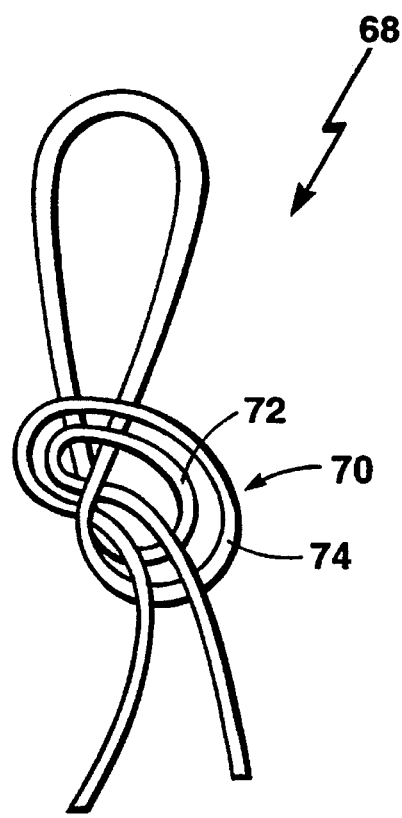
FIG. 4 shows an alternative slip knot arrangement for the thread.

Referring to FIG. 4, an alternative useful slip knot 68 is shown wherein the knot portion 70 is formed from two strands 72 and 74.

Figure 5:
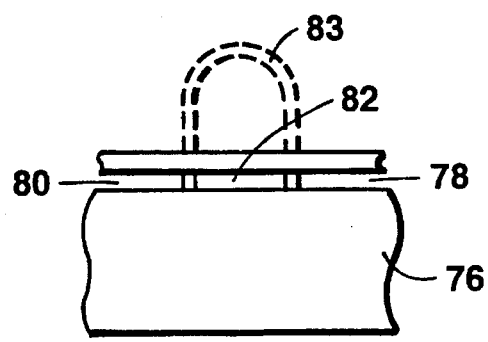
FIG. 5 shows an alternative structure from the plate portion of the structure of this invention.

In an alternative embodiment, as shown in FIG. 5, the through hole for the strand in plate 76 can comprise slots 78 and 80 into which an endless strand such as a rubber band 82 can fit. The strand forms loop 83 which can be fit around one or more teeth.

I claim:

1. A periodontal packing device which comprises:

a plate of a size and shape suitable for insertion into a desired area of an oral cavity of a patient, said plate having a first set of holes of a size for passing a strand therethrough, and a strand selected from the group consisting of a rubber band and a thread having two ends, each of said ends being positioned through one of said first set of holes to form a loop of said strand adjacent one surface of said plate and to position said ends adjacent a second surface of said plate.

2. The device of claim 1 wherein said plate includes a second set of at least one through hole.

3. The device of claim 1 wherein said plate includes a second set of a plurality of through holes.

4. The device of claim 1 wherein said ends are tied together as a slip knot.

5. The device of claim 2 wherein said ends are tied together as a slip knot.

6. The device of claim 3 wherein said ends are tied together as a slip knot.

7. The device of claim 1 wherein said strand comprises a thread coated with a wax composition.

8. The device of claim 2 wherein said strand comprises a thread coated with a wax composition.

9. The device of claim 3 wherein said strand comprises a thread coated with a wax composition.

10. The device of claim 4 wherein said strand comprises a thread coated with a wax composition.

11. A periodontal packing device which comprises:

a plate of a size and shape suitable for insertion into a desired area of an oral cavity of a patient, said plate having a first set of holes of a size for passing a strand therethrough, and an endless strand selected from the group consisting of a rubber band and a thread positioned through said first set of said through holes to form a loop of said strand adjacent one surface of said plate.

12. The device of claim 11 wherein said plate includes a second set of at least one through hole.

13. The device of claim 11 wherein said plate includes a second set of a plurality of through holes.

14. The device of claim 11 wherein said strand comprises a thread coated with a wax composition.

15. The device of claim 12 wherein said strand comprises a thread coated with a wax composition.

16. The device of claim 13 wherein said strand comprises a thread coated with a wax composition.

17. The device of claim 11 wherein said strand comprises a rubber band.

18. The device of claim 12 wherein said strand comprises a rubber band.

19. The device of claim 13 wherein said strand comprises a rubber band.

20. A periodontal packing device which comprises:

a first plate of a size and shape suitable for insertion into a desired area of an oral cavity of a patient, a second plate of a size and shape suitable for insertion into a desired area of an oral cavity of a patient, said first plate having a first set of holes of a size for passing a strand therethrough, a second plate having a second set of holes of a size for passing a strand therethrough, a thread having two ends, each of said ends being positioned through one of said first set of holes and through one of said second set of holes to form a loop of said strand adjacent one surface of said first plate and to position said ends adjacent a second surface of said second plate.

21. The device of claim 20 wherein at least one of said first plate or said second plate includes a third set of at least one through hole.

22. The device of claim 20 wherein said at least one of said first plate or said second plate includes a third set of a plurality of through holes.

23. The device of claim 20 wherein said ends are tied together as a slip knot.

24. The device of claim 21 wherein said ends are tied together as a slip knot.

25. The device of claim 22 wherein said ends are tied together as a slip knot.

26. The device of claim 20 wherein said thread is coated with a wax composition.

27. The device of claim 21 wherein said thread is coated with a wax composition.

28. The device of claim 22 wherein said thread is coated with a wax composition.

29. The device of claim 23 wherein said thread is coated with a wax composition.

30. A periodontal packing device which comprises:

a first plate of a size and shape suitable for insertion into a desired area of an oral cavity of a patient, a second plate of a size and shape suitable for insertion into a desired area of an oral cavity of a patient, a second plate having a second set of holes of a size for passing a strand therethrough, an endless strand selected from the group consisting of a thread and a rubber band positioned through said first set of holes and said second set of holes to form two loops of said strand with one of said loops positioned adjacent one surface of said first plate, and a second set of said loops being positioned adjacent one surface of said second plate.

31. The device of claim 30 wherein said at least one of said first plate or said second plate includes a third set of at least one through hole.

32. The device of claim 30 wherein said at least one of said first plate or said second plate includes a third set of a plurality of through holes.

33. The device of claim 30 wherein said strand comprises a thread coated with a wax composition.

34. The device of claim 31 wherein said strand comprises a thread coated with a wax composition.

35. The device of claim 32 wherein said strand comprises a thread coated with a wax composition.

36. The device of claim 30 wherein said strand comprises a rubber band.

37. The device of claim 31 wherein said strand comprises a rubber band.

38. The device of claim 32 wherein said strand comprises a rubber band.

* * * * *